(12) United States Patent
Chen (10) Patent No.: US 12,121,580 B2
(45) Date of Patent: Oct. 22, 2024

(54) ANTIBACTERIAL PHOTODYNAMIC THERAPY USING COPPER-CYSTEAMINE NANOPARTICLES

(71) Applicant: BOARD OF REGENTS, THE UNIVERSITY OF TEXAS SYSTEM, Austin, TX (US)

(72) Inventor: Wei Chen, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 767 days.

(21) Appl. No.: 16/901,602

(22) Filed: Jun. 15, 2020

(65) Prior Publication Data

US 2020/0390890 A1 Dec. 17, 2020

Related U.S. Application Data

(60) Provisional application No. 62/861,876, filed on Jun. 14, 2019.

(51) Int. Cl.

| | |
|---|---|
| *C09K 17/18* | (2006.01) |
| *A01N 37/02* | (2006.01) |
| *A01N 37/06* | (2006.01) |
| *A01N 55/02* | (2006.01) |
| *A61K 9/51* | (2006.01) |
| *A61K 31/30* | (2006.01) |
| *A61K 41/00* | (2020.01) |
| *A61K 47/12* | (2006.01) |
| *A61N 5/06* | (2006.01) |
| *A61P 31/04* | (2006.01) |
| *B01J 20/22* | (2006.01) |
| *C09K 17/14* | (2006.01) |
| *C12Q 1/14* | (2006.01) |

(52) U.S. Cl.
CPC .......... *A61K 41/0057* (2013.01); *A01N 37/02* (2013.01); *A01N 37/06* (2013.01); *A01N 55/02* (2013.01); *A61K 9/51* (2013.01); *A61K 31/30* (2013.01); *A61K 47/12* (2013.01); *A61N 5/0624* (2013.01); *A61P 31/04* (2018.01); *C12Q 1/14* (2013.01); *A61N 2005/0651* (2013.01); *A61N 2005/0654* (2013.01); *A61N 2005/0661* (2013.01)

(58) Field of Classification Search
CPC ...... A61K 41/0057; A61K 9/51; A61K 31/30; A61K 47/12; A61K 9/0014; A01N 37/02; A01N 37/06; A01N 55/02; A01N 59/12; A01N 59/20; A61N 5/0624; A61N 2005/0651; A61N 2005/0654; A61N 2005/0661; A61N 5/02; A61N 5/10; A61N 2005/1087; A61N 2005/1089; A61N 2005/109; A61N 2005/1098; A61N 5/062; A61P 31/04; C12Q 1/14; Y02A 50/30
See application file for complete search history.

(56) References Cited

U.S. PATENT DOCUMENTS

| | | |
|---|---|---|
| 9,593,131 B2 | 3/2017 | Chen et al. |
| 9,739,897 B2 | 8/2017 | Chen |
| 10,064,942 B2 | 9/2018 | Chen et al. |
| 10,184,079 B2 | 1/2019 | Chen et al. |
| 10,284,936 B2 | 5/2019 | Mao et al. |
| 10,383,940 B2 | 8/2019 | Chen et al. |

FOREIGN PATENT DOCUMENTS

| | | |
|---|---|---|
| CN | 101665696 B | 8/2012 |
| CN | 2014800431246 | 7/2018 |
| EP | 3027182 B1 | 9/2018 |

OTHER PUBLICATIONS

Shrestha, Samana. Use of Radiation to Kill Cancer by Nanoparticles and in a Biodosimeter Using Gene Expression Analysis. Dissertation. University of Rhode Island, 2018. (Year: 2018).*
Ahmad et al. Polyhedron 85 (2015) 239-245. (Year: 2015).*
Liu et al. Scientific Reports, 7, 9290, 2017. (Year: 2017).*
Attie et al. World J Gastroenterol Oct. 14, 2014; 20(38): 13930-13935. (Year: 2014).*
Shreshta et al. PLoS One Dec. 2017(10): e0186169. (Year: 2017).*
Huang et al. Cancer Biology & Therapy 2019, vol. 20, No. 6, 812-825. (Year: 2019).*
Lun Ma et al., "A new Cu-cystamine complex: structure and optical properties," J. Mater. Chem. C, 2014, 2, 4239.
Lun Ma et al., "A New X-Ray Activated Nanoparticle Photosensitizer for Cancer Treatment," Journal of Biomedical Nanotechnology, vol. 10, 1501-1508 (2014).
Casciaro, i et al., "Manual of Clinical Oncology" Dennis A. Casciato, ed. 6th edition.
Lan Ying Wen et al., "Therapeutic effects of systemic photodynamic therapy in a leukemia animal model using A20 cells," Lasers Med Sci (2012) 27:445-452.
Xiao Chu, et al., "Exploitation of TiO2 nanoparticle mediated microdynamic therapy on cancer treatment," Nanomedicine: Nanotechnology, Biology,and Medicine 18 (2019) 272-281.

* cited by examiner

*Primary Examiner* — Mina Haghighatian
*Assistant Examiner* — Janice Y Silverman
(74) *Attorney, Agent, or Firm* — FisherBroyles, LLP (57) ABSTRACT

The uses of the disclosed copper-cysteamine (Cu-Cy) complex for methods for treating Gram-positive and Gram-negative infections in subjects and for disinfecting a surface are disclosed. In addition, the disclosed Cy-Cy nanoparticles provide Fenton-like reactions in vivo, in vitro and ex vivo.

6 Claims, 6 Drawing Sheets

ANTIBACTERIAL PHOTODYNAMIC THERAPY USING COPPER-CYSTEAMINE NANOPARTICLES

FIELD OF THE INVENTION

The uses of the disclosed copper-cysteamine (Cu-Cy) complex for methods for treating Gram-positive and Gram-negative infections in subjects and for disinfecting a surface are disclosed. In addition, the disclosed Cy-Cy nanoparticles provide Fenton-like reactions in vivo, in vitro and ex vivo.

BACKGROUND

Antimicrobial photodynamic inactivation (aPDI) has gained prominence as an alternative non-antibiotic technique to destroy pathogenic microbes of all classes, including Gram-positive and Gram-negative bacteria, fungal cells, viruses and parasites. Its effectiveness is not dependent on the antibiotic-resistance status of the microbes, and it has not been shown to induce any resistance itself despite repeated efforts to do so. Because the microbial killing function is only activated under light illumination, aPDI is safer than disinfectants, and moreover can be used in vivo to treat localized infections and has been used clinically. aPDI involves the light-activated production of reactive oxygen species (ROS) by the interaction of molecular oxygen with the excited state of the photosensitizer (PS). Most PS are dyes with an extensively conjugated system of unsaturated double bonds that provides a large absorption peak in the visible region of the spectrum, and a good quantum yield of the excited singlet state. Intersystem crossing to a long-lived excited triplet state, allows reaction with oxygen to occur, either by an energy transfer Type II mechanism to produce singlet oxygen, or by an electron transfer Type I mechanism to produce superoxide, hydrogen peroxide and hydroxyl radicals. Both singlet oxygen and hydroxyl radicals are highly reactive and can damage lipids, proteins and nucleic acids leading to cell death.

It was found in 1990 that Gram-positive bacteria were exceptionally sensitive to aPDI mediated by a large variety of PS, while Gram-negative bacteria were only sensitive to killing by PS with a pronounced cationic charge. The double cell wall of Gram-negative bacteria provides a barrier against penetration of anionic and neutral charged PS and also against extracellular-generated singlet oxygen. In addition to traditional PS (phenothiazinium dyes, porphyrins, and phthalocyanines,) there is another light-activated process that can kill microbial cells, known as photocatalysis. Photocatalysis relies on nanoparticles that act as large bandgap semiconductors that are excited by short wavelength light (mainly UVA and blue light) to produce ROS (hydroxyl radicals, hydrogen peroxide and singlet oxygen) for bacteria destruction. The most well studied example is titanium dioxide nanoparticles such as the 25 nm diameter P25. Photocatalysis mediated by $TiO_2$ NPs has been shown to kill a variety of pathogenic microorganisms.

DETAILED DISCLOSURE

The materials, compounds, compositions, articles, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

The terms "a" and "an" are defined as one or more unless this disclosure explicitly requires otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Values expressed as "greater than" do not include the lower value. For example, when the "variable x" is defined as "greater than zero" expressed as "0<x" the value of x is any value, fractional or otherwise that is greater than zero.

Similarly, values expressed as "less than" do not include the upper value. For example, when the "variable x" is defined as "less than 2" expressed as "x<2" the value of x is any value, fractional or otherwise that is less than 2.

"Optional" or "optionally" means that the subsequently described event or circumstance can or cannot occur, and that the description includes instances where the event or circumstance occurs and instances where it does not.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Compositions

Disclosed herein are compositions, comprising a compound having the formula:

wherein R is —CH$_2$CH$_2$NH$_2$. The terms "copper-cysteamine," "Cu-Cy material," "Cu-Cy complex," "Cu-Cy," "disclosed material," "disclosed complex," "disclosed compound" and the like are used herein interchangeably throughout the present disclosure to represent the above-identified chemical compound. As disclosed in U.S. Pat. No. 9,593,131 issued Feb. 22, 2017, the compound can have various forms depending upon the method of preparation employed by the formulator. The present disclosure does not exclude any morphology, crystalline form and the like.

The disclosed Cu-Cy nanoparticles can be fabricated to various size ranges depending upon many clinical factors, for example, the type of bacteria, the size of the bacterial cluster, the concentration of the bacteria, the site of treatment, and the like.

In one aspect the nanoparticles can be extremely small in size from about 0.5 nm to about 1.00 nm, for example, 0.5 nm, 0.51 nm, 0.52 nm, 0.53 nm, 0.54 nm, 0.55 nm, 0.56 nm, 0.57 nm, 0.58 nm, 0.59 nm, 0.6 nm, 0.61 nm, 0.62 nm, 0.63 nm, 0.64 nm, 0.65 nm, 0.66 nm, 0.67 nm, 0.68 nm, 0.69 nm, 0.7 nm, 0.71 nm, 0.72 nm, 0.73 nm, 0.74 nm, 0.75 nm, 0.76 nm, 0.77 nm, 0.78 nm, 0.79 nm, 0.8 nm, 0.81 nm, 0.82 nm, 0.83 nm, 0.84 nm, 0.85 nm, 0.86 nm, 0.87 nm, 0.88 nm, 0.89 nm, 0.9 nm, 0.91 nm, 0.92 nm, 0.93 nm, 0.94 nm, 0.95 nm, 0.96 nm, 0.97 nm, 0.98 nm, 0.99 nm, or 1.00 nm.

In addition, the nanoparticles can have any size from about 1.0 nm to about 100 nm. For example, in one iteration the nanoparticles can have any size from about 10.0 nm to about 50 nm. In another iteration the nanoparticles can have any size about 50.0 nm to about 100 nm. In a further iteration the nanoparticles can have any size about 25.0 nm to about 75.0 nm.

In another aspect the nanoparticles can have a size from about 100 nm to about 200 nm, for example, 100 nm, 101 nm, 102 nm, 102 nm, 104 nm, 105 nm, 106 nm, 107 nm, 108 nm, 109 nm, 110 nm, 111 nm, 112 nm, 113 nm, 114 nm, 115 nm, 116 nm, 117 nm, 118 nm, 119 nm, 120 nm, 121 nm, 122 nm, 123 nm, 124 nm, 125 nm, 126 nm, 127 nm, 128 nm, 129 nm, 130 nm, 131 nm, 132 nm, 133 nm, 134 nm, 135 nm, 136 nm, 137 nm, 138 nm, 139 nm, 140 nm, 141 nm, 142 nm, 143 nm, 144 nm, 145 nm, 146 nm, 147 nm, 148 nm, 149 nm, 150 nm, 151 nm, 152 nm, 153 nm, 154 nm, 155 nm, 156 nm, 157 nm, 158 nm, 159 nm, 160 nm, 161 nm, 162 nm, 163 nm, 164 nm, 165 nm, 166 nm, 167 nm, 168 nm, 169 nm, 170 nm, 171 nm, 172 nm, 173 nm, 174 nm, 175 nm, 176 nm, 177 nm, 178 nm, 179 nm, 180 nm, 181 nm, 182 nm, 183 nm, 184 nm, 185 nm, 186 nm, 187 nm, 188 nm, 189 nm, 190 nm, 191 nm, 192 nm, 193 nm, 194 nm, 195 nm, 196 nm, 197 nm, 198 nm, 199 nm, or 200 nm.

In a further aspect the nanoparticles can have a size from about 200 nm to about 300 nm, for example, 200 nm, 201 nm, 202 nm, 202 nm, 204 nm, 205 nm, 206 nm, 207 nm, 208 nm, 209 nm, 210 nm, 211 nm, 212 nm, 213 nm, 214 nm, 215 nm, 216 nm, 217 nm, 218 nm, 219 nm, 220 nm, 221 nm, 222 nm, 223 nm, 224 nm, 225 nm, 226 nm, 227 nm, 228 nm, 229 nm, 230 nm, 231 nm, 232 nm, 233 nm, 234 nm, 235 nm, 236 nm, 237 nm, 238 nm, 239 nm, 240 nm, 241 nm, 242 nm, 243 nm, 244 nm, 245 nm, 246 nm, 247 nm, 248 nm, 249 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm, 281 nm, 282 nm, 283 nm, 284 nm, 285 nm, 286 nm, 287 nm, 288 nm, 289 nm, 290 nm, 291 nm, 292 nm, 293 nm, 294 nm, 295 nm, 296 nm, 297 nm, 298 nm, 299 nm, or 300 nm.

In a still further aspect the nanoparticles can have a size from about 300 nm to about 400 nm, for example, 300 nm, 301 nm, 302 nm, 302 nm, 304 nm, 305 nm, 306 nm, 307 nm, 308 nm, 309 nm, 310 nm, 311 nm, 312 nm, 313 nm, 314 nm, 315 nm, 316 nm, 317 nm, 318 nm, 319 nm, 320 nm, 321 nm, 322 nm, 323 nm, 324 nm, 325 nm, 326 nm, 327 nm, 328 nm, 329 nm, 330 nm, 331 nm, 332 nm, 333 nm, 334 nm, 335 nm, 336 nm, 337 nm, 338 nm, 339 nm, 340 nm, 341 nm, 342 nm, 343 nm, 344 nm, 345 nm, 346 nm, 347 nm, 348 nm, 349 nm, 350 nm, 351 nm, 352 nm, 353 nm, 354 nm, 355 nm, 356 nm, 357 nm, 358 nm, 359 nm, 360 nm, 361 nm, 362 nm, 363 nm, 364 nm, 365 nm, 366 nm, 367 nm, 368 nm, 369 nm, 370 nm, 371 nm, 372 nm, 373 nm, 374 nm, 375 nm, 376 nm, 377 nm, 378 nm, 379 nm, 380 nm, 381 nm, 382 nm, 383 nm, 384 nm, 385 nm, 386 nm, 387 nm, 388 nm, 389 nm, 390 nm, 391 nm, 392 nm, 393 nm, 394 nm, 395 nm, 396 nm, 397 nm, 398 nm, 399 nm, or 400 nm.

In a yet further aspect the nanoparticles can have a size from about 400 nm to about 500 nm, for example, 400 nm, 401 nm, 402 nm, 402 nm, 404 nm, 405 nm, 406 nm, 407 nm, 408 nm, 409 nm, 410 nm, 411 nm, 412 nm, 413 nm, 414 nm, 415 nm, 416 nm, 417 nm, 418 nm, 419 nm, 420 nm, 421 nm, 422 nm, 423 nm, 424 nm, 425 nm, 426 nm, 427 nm, 428 nm, 429 nm, 430 nm, 431 nm, 432 nm, 433 nm, 434 nm, 435 nm, 436 nm, 437 nm, 438 nm, 439 nm, 440 nm, 441 nm, 442 nm, 443 nm, 444 nm, 445 nm, 446 nm, 447 nm, 448 nm, 449 nm, 450 nm, 451 nm, 452 nm, 453 nm, 454 nm, 455 nm, 456 nm, 457 nm, 458 nm, 459 nm, 460 nm, 461 nm, 462 nm, 463 nm, 464 nm, 465 nm, 466 nm, 467 nm, 468 nm, 469 nm, 470 nm, 471 nm, 472 nm, 473 nm, 474 nm, 475 nm, 476 nm, 477 nm, 478 nm, 479 nm, 480 nm, 481 nm, 482 nm, 483 nm, 484 nm, 485 nm, 486 nm, 487 nm, 488 nm, 489 nm, 490 nm, 491 nm, 492 nm, 493 nm, 494 nm, 495 nm, 496 nm, 497 nm, 498 nm, 499 nm, or 500 nm.

Figure 1:
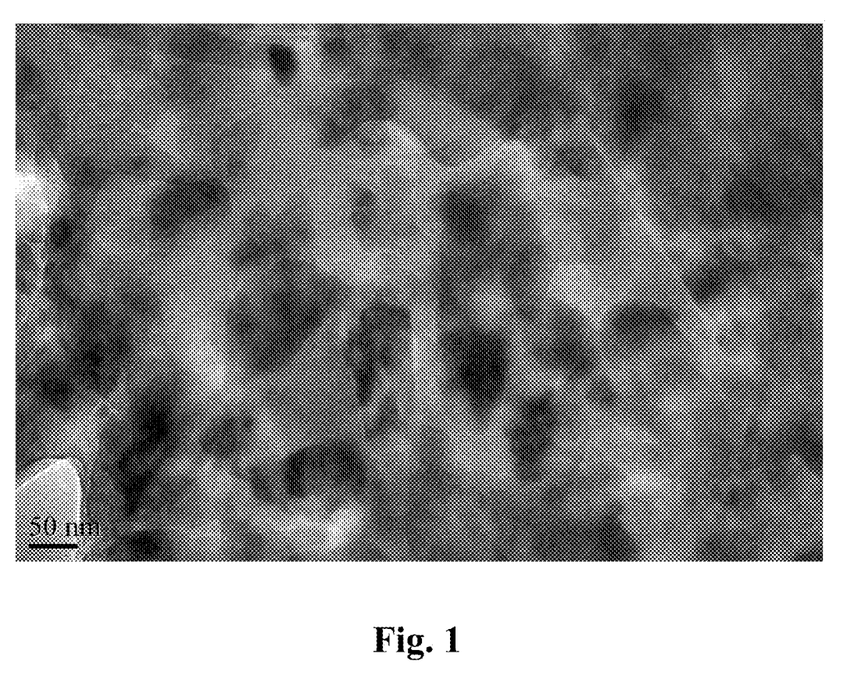
FIG. 1 is a TEM image of a polyethylene glycol coated Cu-Cy nanoparticle.
Figure 2:
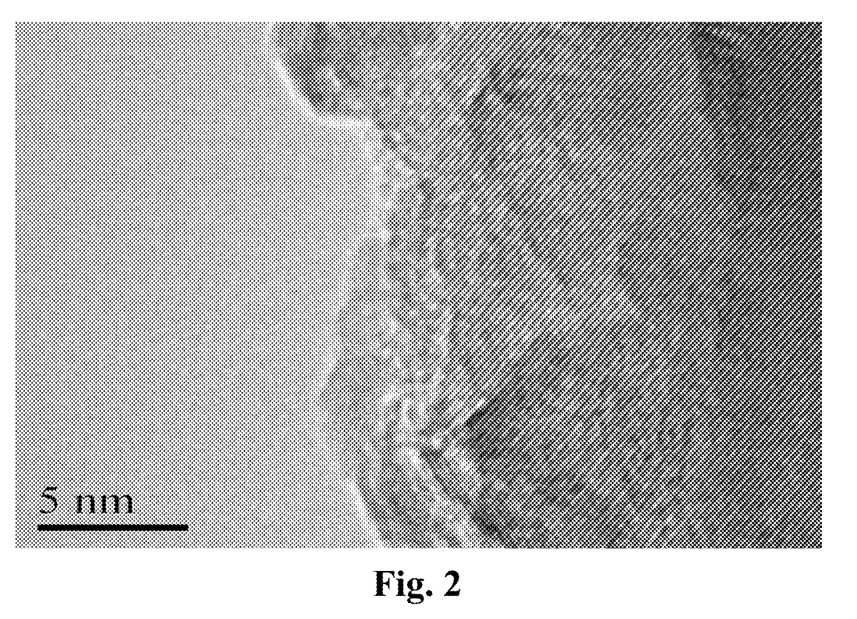
FIG. 2 shows the 0.227 nm lattice spacing of the nanoparticle of FIG. 1.
Figure 7:
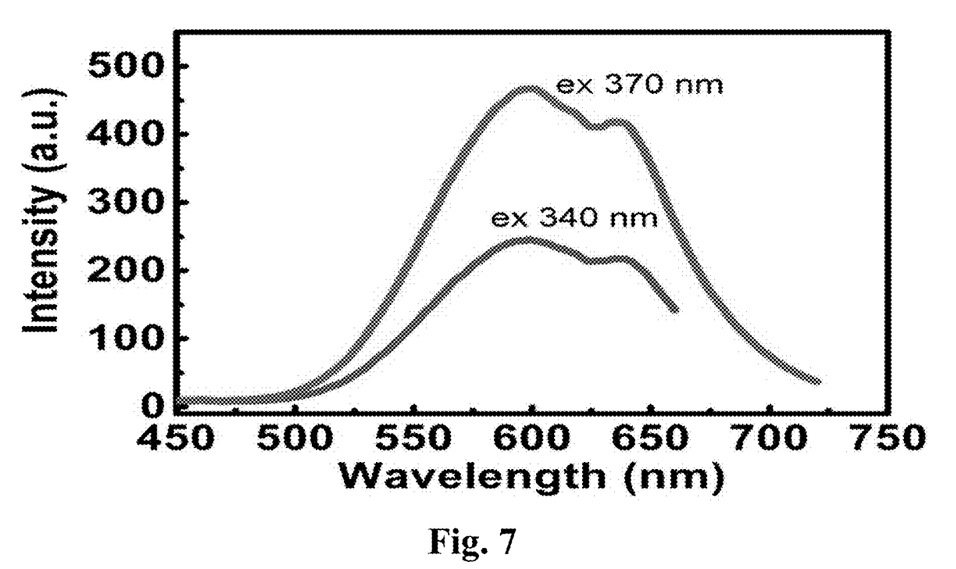
FIG. 7 shows the emission spectra of the disclosed compound having doublet peaks at 607 and 633 nm.

The disclosed Cu-Cy NPs structure includes two different Cu atoms-Cu(1) and Cu(2) (they are both $Cu^+$ ions), which bind to 4 and 3 other atoms respectively. Cu-Cy NPs can display intense photoluminescence and X-ray luminescence. The detail of crystal structure and optical properties of Cu-Cy NPs were described in our previous paper (See, Ma, L., et al., (2014) "A new Cu-cysteamine complex: structure and optical properties," *J. Mater. Chem. C* 2(21), pp 4239-4246). For the samples used for this study, they were coated with polyethylene glycol and their size is about 70-110 nm as judged from their TEM images as shown in FIG. 1. The lattice spacing measured from the image is 0.227 nm (FIG. 2). The particles have a strong red luminescence as displayed in FIG. 3. The emission spectra have doublet peaks at 607 and 633 nm as shown in FIG. 7. Two emission peaks are from the two types of copper ions, i.e., Cu(1) and Cu(2), which differ from each other by different coordination. The longer wavelength (633 nm) emission is related to Cu(1) as it has shorter distances to neighboring copper ions (2.81° A and 2.89° A) compared to the distances of Cu(2) and its neighboring copper ions (3.31° A and 3.74° A); consequently, the 607 nm emission is assigned to Cu(2) ions.

Figure 3:
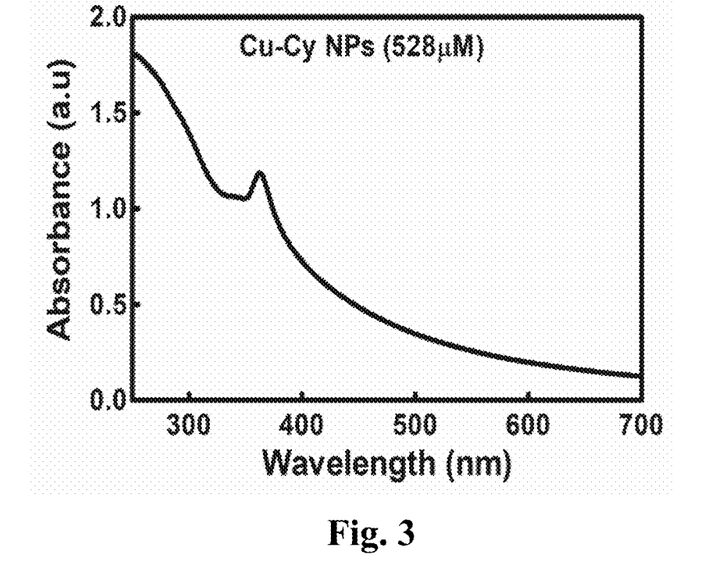
FIG. 3 shows the optical absorption spectrum of Cu-Cy NPs at 528 µM in water.
Figure 4:
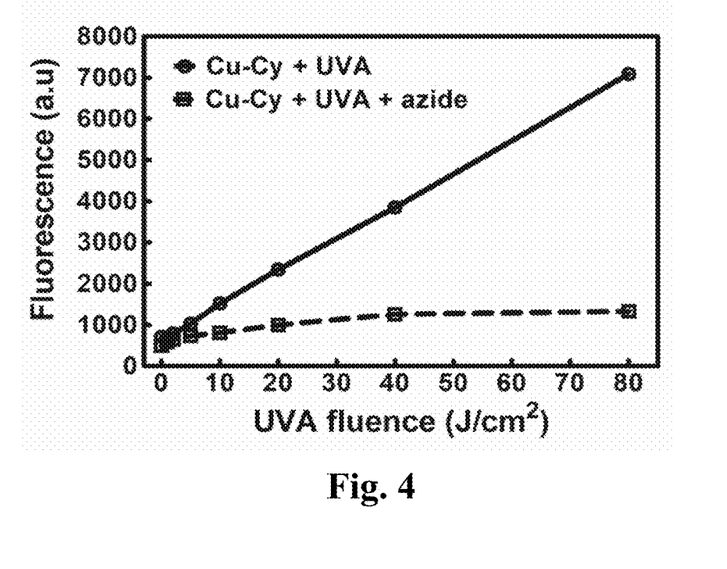
FIG. 4 shows the light dose-dependent production of $H_2O_2$ when 10 µM was irradiated with 360 nm UVA light, using the Amplex Red assay.

FIG. 3 shows the optical absorption spectrum of Cu-Cy NPs at 528 μM in water. Cu-Cy NPs have a strong absorption in the UV range with a strong peak at 365 nm but almost no absorption in the visible range, which makes Cu-Cy distinct from other photosensitizers like porphyrins which have strong absorptions in both UV and visible ranges. [26] The strong absorption in UV range makes it possible to combine with UV for treating bacteria or virus because UV is widely used for sterilization. The absence of absorption in visibility makes it devoid of toxicity or side-effects from sunshine or room light, which has been a concern for photodynamic therapy on practical applications One significant advantage the disclosed methods have is that they are not subject to bacterial antimicrobial resistance. Therefore, when commonly used antibiotics are ineffective because of acquired resistance, the disclosed methods are capable of functioning to kill targeted bacteria.

In one aspect, the disclosed compositions comprise:
a) copper-cysteamine having the formula:

wherein R is —$CH_2CH_2NH_2$; and
b) one or more pharmaceutically acceptable ingredients.

In one embodiment of this aspect the composition includes a means for lowering the pH of the composition, for example, including an aqueous solution of an acid that lowers the pH of the composition. In one iteration of this embodiment the composition is capable of exhibiting Fenton-like reactions.

A non-limiting embodiment of this aspect, the disclosed compositions comprise:
a) copper-cysteamine having the formula:

$$Cu_3Cl(SR)_2$$

wherein R is —$CH_2CH_2NH_2$; and
b) an organic acid;
wherein the pH of the composition is from about 3.0 to about 7.0.

Non-limiting examples of organic acids includes acetic acid, lactic acid, citric acid, oxalic acid, malic acid, maleic acid, tartaric acid, glycolic acid, propionic acid, malonic, or fumaric acid.

In one iteration the pH is from about 6.0 to about 6.9. In a further iteration, the pH is from about 6.0 to about 6.5. In another iteration the pH is from about 4.0 to about 5.5. In a still further iteration the pH is from about 5.5 to about 6.5. In a still further iteration the pH is from about 3.0 to about 4.5. The disclosed compositions can have a pH of 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 50, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or 7.0. As such, the compositions can have a pH lower than physiological pH.

Without wishing to be limited by theory, the differences between Gram-positive verse Gram-negative bacteria are primarily related to their cell wall composition. Gram-positive bacteria have cell walls composed mostly of a substance unique to bacteria known as peptidoglycan. Gram-negative bacteria have cell walls with only a thin layer of peptidoglycan and an outer membrane with a lipopolysaccharide component not found in Gram-positive bacteria. Gram-negative bacteria contain three principal layers: the outer membrane (OM), the peptidoglycan cell wall, and the inner membrane (IM). They comprise a major proportion of drug resistant pathogens and display a complex envelope with an outer (OM) and an inner (IM) membrane delimiting a periplasmic space. This cellular organization results in the presence of various protein channels involved in the transport, uptake or efflux, of a large variety of compounds, nutrients or toxic molecules (sugars, drugs, small peptides, chemicals). The outer membrane is the first line of defense for Gram-negative bacteria against toxic compounds. This barrier is impermeable to large, charged molecules. Influx is largely controlled by porins, which are water-filled open channels that span the outer membrane and allow the passive penetration of hydrophilic molecules. Bacterial pathogenicity is largely dependent on its surface structures. Among the components of the bacterial outer membrane, outer membrane proteins (OMPs), such as the porins, play a fundamental role in pathogenicity and in protection and represent useful targets for therapeutic development. Porins are involved in the exchange of nutrients over the outer membrane of Gram-negative bacteria but are also involved in pathogenesis. The OM is a characteristic feature of Gram-negative bacteria, which Gram-positive bacteria lack. This structure provides the reason for the distinct the behaviors of the two bacteria.

Nanoparticle Coating, Surface Charges, Size and Penetration:

Bacterial cell walls have a negative charge. In Gram positive bacteria the reason of this negative charge is the presence of teichoic acids linking the peptidoglycan to the underlying plasma membrane. These teichoic acids are negatively charged because of the presence of phosphate in their stricture. The Gram negative bacteria have an outer covering of phospholipids and Lipopolysaccharides. The lipopolysaccharides impart a strongly negative charge to surface of Gram negative bacterial cells. Therefore, cationic nanoparticles have a superiority for killing Gram-negative cells, though cationic PS are often much better at killing Gram-positive bacteria compared to Gram-negatives. It has been proposed that the cationic PS penetrate the outer membrane of Gram-negatives by the "self-promoted uptake pathway" in which the divalent metal cations $Ca^{2+}$ and $Mg^{2+}$ are gradually displaced by the PS, and the lipopolysaccharide in the outer membrane permeability barrier is destabilized. Cu-Cy NPs were coated with poly(ethylene glycol) methyl ether thiol, therefore, their surfaces are negatively charged, making them difficult to attach to the bacterial membranes or cell walls. This is one of the reasons that the killing of gram-negative bacteria is not easily accomplished. Secondly, the Cu-Cy NPs were not able to penetrate the cell walls because their size was too large. General bacterial porins are a family of protein from the outer membranes of Gram-negative bacteria. The porins act as molecular filters for hydrophilic compounds. They are responsible for the 'molecular sieve' properties of the outer membrane. Porins form large water-filled channels which allow the diffusion of hydrophilic molecules into the periplasmic space. In Gram-negative bacteria, the inner membrane is the major permeability barrier. The outer membrane is more permeable to hydrophilic substances, due to the presence of porins. Porins have threshold sizes of transportable molecules that depend on the type of bacteria and porin. Generally, only substances less than 600 Daltons or about 2 nm in size can diffuse through. The Cu-Cy particles disclosed herein are from about 70 nm to about 110 nm in size, which are much larger than the channels of porins, therefore cannot go through the porin channels. Therefore, the majority of killing is due to the ROS produced by Cu-Cy NPs upon light activation Singlet Oxygen, Hydrogen Peroxide, Penetration and Inactivation:

As demonstrated herein, we have shown that Cu-Cy NPs produced singlet oxygen and $H_2O_2$ under UV activation at 360 nm. The damages by singlet oxygen or/and $H_2O_2$ are a major reason in killing the bacteria as it has been reported that singlet oxygen or $H_2O_2$ could directly kill both gram-positive and gram-negative bacteria. The gram-negative bacterial cell wall lipopolysaccharide coat (LPS) offers some protection from the toxic effects of exogenous agents. Most gram-positive bacteria lack a protective structure analogous to the gram-negative LPS and the outer membrane in which it is anchored. In addition, possibly forming a structural barrier to penetration, this outer membrane may form a chemical trap for singlet oxygen; it is composed of unsaturated fatty acids and proteins, which are compounds known to react chemically with singlet oxygen. The outer membrane and LPS of gram-negative bacteria do not, however, represent vital targets for the lethal action of singlet oxygen, since these can be removed without killing the cells (spheroplast formation) (see, A. Dahl, et al., *J Bacterial*, 1989, 171, 2188-2194). Because the cell wall structure of gram-positive and gram-negative bacteria represents the fundamental difference between these cells, once the barrier is crossed by singlet oxygen, the targets and mechanisms for cell killing for both gram-positive and gram-negative bacteria would be similar or identical. As discussed in Dahl et al., in gram-negative bacteria, singlet oxygen reaching the outer membrane-LPS portion of the cell wall can either collide without penetration or reaction, react with the components of the outer membrane, or penetrate through the various layers to the vital target. Reaction with the outer membrane components can lead to generation of reactive secondary products, such as peroxy radicals, which may in turn be able to cause lethal damage to the vital target. The total toxicity, then, is be the sum of the singlet oxygen reaching the inner membrane and the lethal effects of secondary reaction products from the outer membrane. For gram-positive bacteria, singlet oxygen can diffuse easily through the relatively open structure of the peptidoglycan layer of the cell wall to react with the vital target. The rate of killing depends only on direct singlet oxygen-vital target interactions, without any need to invoke secondary reaction mechanisms such as in the gram-negative outer membrane. This can explain quite well why Cu-Cy NPs are much more effective in killing gram-positive bacteria than gram-negative bacteria because singlet oxygen is the major ROS products produced by Cu-Cy NPs under UV excitation as a result of energy transfer process. Even though $H_2O_2$ was detected by the Amplex Red assay, it is not the major product as it is the byproducts of singlet oxygen as illustrated in eq. (1) The reaction of (1) is only possible in acidic conditions like in a tumor environment.

As mentioned herein above the composition can exhibit Fenton-like activity which aids in achieving anti-bacterial activity. This activity is obtained using the copper atoms of the disclosed copper-cysteamine nanoparticles.

Fenton-Like Reactions/Activity

Fenton reactions refer to the process in which Fe and its salts catalyze the conversion of $H_2O_2$ to $^\cdot OH$. If other cations, such as Cu, Ag, Mn, and Au, participate in the catalytic conversion, then such reactions are referred to as Fenton-like reaction. Considering elevated levels of $H_2O_2$ and slightly acidic pH in TME, Fenton and Fenton-like reactions can be exploited to achieve highly selective cancer treatment. In recent years, several redox-active nano-formulations, mainly iron-based, were designed and investigated for their potential in Fenton reactions mediated cancer treatment modalities.

Without wishing to be limited by theory, Fe-based Fenton reagents, however, are optimally effective only in low pH conditions (pH<4) that are beyond what would be encountered in their applied biological context, thereby limiting their practicality in future clinical settings. Consequently, most Fe-based Fenton reagents require exogenous additives, including ascorbic acid and $H_2O_2$ to achieve a desired therapeutic outcome. Additionally, these nanocatalysts required administration at high doses in order to achieve desired therapeutic outcomes.

The disclosed Cu-based materials are regarded as an efficient Fenton catalyst at circumneutral pH and have thus been considered excellent candidates to be the basis for developing new cancer treatments (see, Lee H et al., "PH-Dependent Reactivity of Oxidants Formed by Iron and Copper-Catalyzed Decomposition of Hydrogen Peroxide," *Chemosphere* 2013, 92 (6), 652-658). Also, the highest reaction rate of $Cu^{1+}$ with $H_2O_2$ ($10^4$ $M^{-1}s^{-1}$) is higher than that of $Fe^{2+}$ (63 $M^{-1}s^{-1}$). Among reported catalysts, heterogeneous Fenton-like catalysts show great promise as they can generate $^\cdot OH$ in the targeted region without leaching free metal ions, thereby avoiding unwanted toxicity.

Ma (Ma, B. et al., "Self-Assembled Copper-Amino Acid Nanoparticles for in Situ Glutathione "AND" H 2 O 2 Sequentially Triggered Chemodynamic Therapy," *J. Am. Chem. Soc.* 2019, 141 (2), 849-857) developed a promising $Cu^{2+}$ based heterogenous nano-catalyst that can be activated by GSH and $H_2O_2$ following a logic "AND" gate, however, this catalyst requires a high dose of 200 μg/mL for optimum efficacy. Higher levels of copper could cause damage to vital organs, including the brain and liver. Therefore, if Cu-based catalysts are to be used for cancer therapy, then a way to lower their effective dose such that they may be physiologically tolerable. One way to improve the efficiency of a heterogenous Cu-based catalyst is developing the catalyst that has copper in its reduced state ($Cu^{1+}$) rather than in its oxidized state ($Cu^{2+}$) as the reaction rate of $Cu^{1+}$ is approximately 22 times faster than that of $Cu^{2+}$.

$$Cu^{1+}+H_2O_2 \rightarrow Cu^{2+}+\cdot OH+OH^- \quad (k=1\times 10^4 \ M^{-1}S^{-1})$$

$$Cu^{2+}+H_2O_2 \rightarrow Cu^{1+}+\cdot HO_2^-+H^+ \quad (k=460 \ M^{-1}S^{-1})$$

As disclosed herein, copper-cysteamine nanoparticle (Cu-Cy NP) comprise $Cu^{1+}$ instead of $Cu^{2+}$, which can be stimulated by X-ray, UV-light, microwave, and ultrasound to produce various types of ROS for cancer treatment. Furthermore, Cu-Cy, as disclosed herein, can be used to inactivate both Gram-positive and Gram-negative bacteria upon UV light activation. Because the Cu-Cy NP can be activated by multiple excitation sources, demonstrates that it is a candidate for photodynamic therapy to combat cancer.

In another aspect, the disclosed compositions comprise:
a) copper-cysteamine having the formula:

$$Cu_3Cl(SR)_2$$

wherein R is —$CH_2CH_2NH_2$;
b) one or more halogen salts; and
c) one or more pharmaceutically acceptable ingredients or carriers.

In one embodiment of this aspect, the halogen salt is an alkali metal salt of a halogen.

In one non-limiting iteration the compositions comprise:
a) copper-cysteamine having the formula:

$$Cu_3Cl(SR)_2$$

wherein R is —$CH_2CH_2NH_2$;
b) potassium iodide; and
c) a carrier.

Without wishing to be limited by theory, the mechanism behind the killing enhancement for the combination of Cu-Cy when KI is added is due to the formation of iodine triion and hydrogen peroxide from the reaction of singlet oxygen and iodine molecules formed upon irradiation of the Cu-Cy.

Methods

In one aspect the disclosed methods, comprise:
a) administering to a subject having a bacterial infection an effective amount of nanoparticles containing a compound having the formula:

$$Cu_3Cl(SR)_2$$

wherein R is —$CH_2CH_2NH_2$ such that the bacteria are in contact with the compound; and
b) exposing the compound to a photo-activating amount of electromagnetic radiation at a wavelength that actives the compound.

In another aspect the disclosed method, comprises:
a) administering to a subject having a Gram-positive bacterial infection an effective amount of nanoparticles containing a compound having the formula:

$$Cu_3Cl(SR)_2$$

wherein R is —$CH_2CH_2NH_2$ such that the Gram-positive bacteria are in contact with the compound; and
b) exposing the compound to a photo-activating amount of electromagnetic radiation at a wavelength that actives the compound.

In a still further aspect the disclosed method, comprises:
a) administering to a subject having a bacterial infection an effective amount of a composition containing:
i) nanoparticles containing a compound having the formula:

$$Cu_3Cl(SR)_2$$

wherein R is —$CH_2CH_2NH_2$; and
ii) a halide containing salt;
such that the bacteria are in contact with the composition; and
b) exposing the compound to a photo-activating amount of electromagnetic radiation at a wavelength that actives the compound.

In one embodiment of this aspect the method, comprises:
a) administering to a subject having a bacterial infection an effective amount of a composition containing:
i) nanoparticles containing a compound having the formula:

$$Cu_3Cl(SR)_2$$

wherein R is —$CH_2CH_2NH_2$; and
ii) potassium iodide;
such that the bacteria are in contact with the composition; and
b) exposing the compound to a photo-activating amount of electromagnetic radiation at a wavelength that actives the compound.

In further aspect the disclosed method, comprises administering to a subject having a Gram-positive bacterial infection an effective amount of a composition comprising:
i) a nanoparticle containing a compound having the formula:

$$Cu_3Cl(SR)_2$$

wherein R is —$CH_2CH_2NH_2$ such that the Gram-positive bacteria are in contact with the compound; and
ii) a carrier having a pH of from about 3 to about 7.

The disclosed methods which do not rely on irradiation of the nanoparticles rely on Fenton-like reactions.

What is meant herein by "activates the compound" is that an aqueous solution of the disclosed nanoparticles when exposed to electromagnetic radiation, emits singlet oxygen, $^1O_2$. As described herein below this singlet oxygen besides interacting with the cellular walls of bacteria, also is capable of producing hydrogen peroxide, $H_2O_2$, which is a known and well-studied disinfectant.

In one embodiment the electromagnetic radiation can be from a source of X-rays or from a source of ultraviolet light. The subject's area or targeted site is typically irradiated for a sufficient amount of time to obtain a desired response. The formulator, however, can use any source of radiation, for example, a radiation source chosen from ultra violet light, microwave radiation, an X-ray source, a gamma-ray source, a beta-ray source, a source of proton emission, a source of electron emission, or a source of neutron emission. The desired response is determined by the physician or medical specialist. The treatment can be conducted once or as many times as determined by the physician or medical specialist.

Without wishing to be limited by theory the disclosed Cu-Cy nanoparticles produce singlet oxygen and $H_2O_2$ when exposed to electromagnetic radiation, for example, UV activation at 360 nm. The damage done to Gram-positive cellular structure by singlet oxygen or/and $H_2O_2$ is the reason for bacterial death. Unlike Gram-positive bacteria, the Gram-negative bacterial cell wall lipopolysaccharide coat (LPS) offers some protection from the toxic effects of exogenous agents. Most Gram-positive bacteria lack a protective structure analogous to the gram-negative LPS.

In another aspect of the disclosed methods, without wishing to be limited by theory, the addition of a halide salt, for example, potassium iodide, increases the effectiveness of the Cu-Cy nanoparticles against Gram-negative bacteria. It has been observed that triiodide ion is formed when KI is present and that this combination of singlet oxygen, hydrogen peroxide and triiodide is capable of penetrating the cell walls of Gram-negative bacteria.

In one aspect the disclosed method, comprises:

a) administering to a subject having a bacterial infection an effective amount of nanoparticles containing a compound having the formula:

$$Cu_3Cl(SR)_2$$

wherein R is —$CH_2CH_2NH_2$ such that the bacteria are in contact with the compound; and b) exposing the compound to a photo-activating amount of electromagnetic radiation at a wavelength that actives the compound.

In another aspect the disclosed method, comprises:

a) administering to a subject having a Gram-positive bacterial infection an effective amount of nanoparticles containing a compound having the formula:

$$Cu_3Cl(SR)_2$$

wherein R is —$CH_2CH_2NH_2$ such that the Gram-positive bacteria are in contact with the compound; and b) exposing the compound to a photo-activating amount of electromagnetic radiation at a wavelength that actives the compound.

In a still further aspect the disclosed method, comprises:

a) administering to a subject having a bacterial infection an effective amount of a composition containing:

i) nanoparticles containing a compound having the formula:

$$Cu_3Cl(SR)_2$$

wherein R is —$CH_2CH_2NH_2$; and ii) a halide containing salt;

such that the bacteria are in contact with the composition; and b) exposing the compound to a photo-activating amount of electromagnetic radiation at a wavelength that actives the compound.

In one embodiment of this aspect the method, comprises:

a) administering to a subject having a bacterial infection an effective amount of a composition containing:

i) nanoparticles containing a compound having the formula:

$$Cu_3Cl(SR)_2$$

wherein R is —$CH_2CH_2NH_2$; and ii) potassium iodide;

such that the bacteria are in contact with the composition; and b) exposing the compound to a photo-activating amount of electromagnetic radiation at a wavelength that actives the compound.

In a further aspect the methods include contacting Gram-negative bacteria with an effective amount of a compound having the formula:

$$Cu_3Cl(SR)_2$$

wherein R is —$CH_2CH_2NH_2$.

In one embodiment of this aspect, the method comprises contacting Gram-negative bacteria with a composition, comprising:

a) copper-cysteamine having the formula:

$$Cu_3Cl(SR)_2$$

wherein R is —$CH_2CH_2NH_2$; and b) one or more pharmaceutically acceptable ingredients.

In another embodiment of this aspect, the method comprises contacting Gram-negative bacteria with a composition, comprising:

a) copper-cysteamine having the formula:

$$Cu_3Cl(SR)_2$$

wherein R is —$CH_2CH_2NH_2$; and b) an organic acid;

wherein the pH of the composition is from about 3.0 to about 7.0.

In further embodiment of this aspect, the method comprises contacting Gram-negative bacteria with a composition, comprising:

a) copper-cysteamine having the formula:

$$Cu_3Cl(SR)_2$$

wherein R is —$CH_2CH_2NH_2$;

b) one or more halogen salts; and c) one or more pharmaceutically acceptable ingredients or carriers.

Because the source of electromagnetic radiation can be a topically effective source such as ultra violet radiation, wounds containing Gram-positive bacteria can be treated by non-invasive procedures. For example, a wound infected by Gram-positive bacteria can be exposed to a UV lamp. The radiation level and the time of exposure can be determined by taking a sample of the wound fluid after treatment and analyzing it for the presence, the absence or the amount of bacteria present.

The Gram-positive bacteria can be either cocci or bacilli. Non-limiting examples of Gram-positive cocci include

*Streptococcus pyogenes, Streptococcus agalactiae, Streptococcus faecalis, Streptococcus pneumoniae, Staphylococcus aureus*, especially MRSA, and *Enterococcus faecalis*.

The Gram-negative bacteria can be E.

In another aspect of the present disclosure, a method for treating a wound, comprising:

a) identifying the presence of a bacteria in a wound;

b) contacting the wound with the disclosed composition comprising Copper-Cysteamine nanoparticles and optionally comprising a halide salt;

c) exposing the wound to a source of ultra violet light; and d) culturing a sample taken from the wound to determine the presence of the Gram-positive bacteria.

In one embodiment of this method for treating a Gram-positive bacterial wound infection the treatment can be repeated if bacteria are found to be present. In addition, based upon the initial amount present in the wound when compared to a sample taken in step (d), the physician, medical technician, etc. can adjust the UV intensity, the length of treatment or the number of treatments necessary.

A further aspect of the present disclosure relates to methods for disinfecting surfaces exposed to Gram-positive bacteria. In one embodiment the disclosed method, comprises:

a) applying to a surface containing bacteria an effective amount of nanoparticles containing a compound having the formula:

wherein R is —CH$_2$CH$_2$NH$_2$ such that the Gram-positive bacteria are in contact with the compound and potassium iodide; and b) exposing the compound to a photo-activating amount of electromagnetic radiation at a wavelength that activates the compound.

In the case of *Enterococcus faecalis*, this bacteria presents itself commonly in hospital settings wherein patients already have compromised immune systems. The same is true with Methicillin-resistant *Staphylococcus aureus* which is extremely difficult to treat. As such, compositions comprising the Cu-Cy nanoparticles can be sprayed onto the open surfaces of a hospital environment, including operating rooms; stretchers; wheelchairs; patient rooms and the like, then the surface is irradiated by UV light to kill the bacteria.

Further disclosed are compositions comprising the disclosed Cu-Cy nanoparticles. The nanoparticles can be effectively dispersed in water. In one embodiment; to aid in dispersion of the nanoparticles, the particles can be combined with a dispersant.

The concentration of the nanoparticles in all aspects and embodiments disclosed herein can be from about 1 µM to about 100 µM. In one embodiment the concentration can be from about 1 µM to about 100 µM. In another embodiment the concentration can be from about 50 µM to about 100 µM. In a further embodiment the concentration can be from about 70 µM to about 100 µM. In a yet further embodiment the concentration can be from about 90 µM to about 100 µM. The concentration can have any value from about 1 µM to about 100 µM, for example, 1 µM, 2 µM, 3 µM, 4 µM, 5 µM, 6 µM, 7 µM, 8 µM, 9 µM 10 µM, 11 µM, 12µ, 13 µM, 14 µM, 15 µM, 16 µM, 17 µM, 18 µM, 19 µM, 20 µM, 21 µM, 22µ, 23 µM, 24 µM, 25 µM, 26 µM, 27 µM, 28 µM, 29 µM, 30 µM, 31 µM, 32µ, 33 µM, 34 µM, 35 µM, 36 µM, 37 µM, 38 µM, 39 µM, 40 µM, 41 µM, 42 µM, 43 µM, 44 µM, 45 µM, 46 µM, 47 µM, 48 µM, 49 µM, 50 µM, 51 µM, 52µ, 53 µM, 54 µM, 55 µM, 56 µM, 57 µM, 58 µM, 59 µM, 60 µM, 61 µM, 62µ, 63 µM, 64 µM, 65 µM, 66 µM, 67 µM, 68 µM, 69 µM, 70 µM, 71 µM, 72 µM, 73 µM, 74 µM, 75 µM, 76 µM, 77 µM, 78 µM, 79 µM, 80 µM, 81 µM, 82µ, 83 µM, 84 µM, 85 µM, 86 µM, 87 µM, 88 µM, 89 µM, 90 µM, 91 µM, 92µ, 93 µM, 94 µM, 95 µM, 96 µM, 97 µM, 98 µM, 99 µM, or 100 µM.

The concentration of potassium iodide in all aspects and embodiments disclosed herein can be from about 1 mM to about 100 mM. In one embodiment the concentration can be from about 1 mM to about 100 mM. In another embodiment the concentration can be from about 50 mM to about 100 mM. In a further embodiment the concentration can be from about 70 mM to about 100 mM. In a yet further embodiment the concentration can be from about 90 mM to about 100 mM. The concentration can have any value from about 1 mM, 2 mM, 3 mM, 4 mM, 5 mM, 6 mM, 7 mM, 8 mM, 9 mM 10 mM, 11 mM, 12 m, 13 mM, 14 mM, 15 mM, 16 mM, 17 mM, 18 mM, 19 mM, 20 mM, 21 mM, 22 m, 23 mM, 24 mM, 25 mM, 26 mM, 27 mM, 28 mM, 29 mM, 30 mM, 31 mM, 32 m, 33 mM, 34 mM, 35 mM, 36 mM, 37 mM, 38 mM, 39 mM, 40 mM, 41 mM, 42 m, 43 mM, 44 mM, 45 mM, 46 mM, 47 mM, 48 mM, 49 mM, 50 mM, 51 mM, 52 m, 53 mM, 54 mM, 55 mM, 56 mM, 57 mM, 58 mM, 59 mM, 60 mM, 61 mM, 62 m, 63 mM, 64 mM, 65 mM, 66 mM, 67 mM, 68 mM, 69 mM, 70 mM, 71 mM, 72 m, 73 mM, 74 mM, 75 mM, 76 mM, 77 mM, 78 mM, 79 mM, 80 mM, 81 mM, 82 m, 83 mM, 84 mM, 85 mM, 86 mM, 87 mM, 88 mM, 89 mM, 90 mM, 91 mM, 92 m, 93 mM, 94 mM, 95 mM, 96 mM, 97 mM, 98 mM, 99 mM, or 100 mM.

Porous surfaces are especially difficult to disinfect. In this instance a more penetrating type of electromagnetic radiation can be used.

EXAMPLE 1

In following example a 365-nm UVA light-emitting diode (LED) light source (Larson Electronics LLC, Kemp, TX) was used. The emission spectrum was measured with a spectroradiometer (SPR-01; Luzchem Research, Inc., Ottawa, Ontario, Canada) and showed a peak emission at 365±5 nm. For all experiments, the irradiance was fixed at 16 mW/cm$^2$ (1 J/cm$^2$ delivered in 1 min), measured by a model IL-1700 research radiometer-photometer (International Light, Inc., Newburyport, MA).

The following microbial strains were used: Gram-positive bacteria, methicillin-resistant *Staphylococcus aureus* (MRSA) US300 and *Enterococcus faecalis* ATCC 29212. A colony of bacteria was suspended in 10 mL of BHI and grown overnight in a shaker incubator (New Brunswick Scientific, Edison, NJ, USA) at 37° C. at 120 rpm under aerobic conditions. An aliquot of 1 mL from an overnight suspension was refreshed in fresh BHI for 2 h at 37° C. to mid-log phase. Cell concentration was estimated by measuring optical density (OD) at 600 nm (OD of 0.8=10$^8$ CFU cells/ml).

Suspensions of bacteria (10$^8$ cells/mL) were incubated with various concentrations (1 µM, 10 µM, 50 µM, 100 µM) of Cu-Cy in the dark at room temperature for 30 min. An aliquot of 100 µL was taken as the dark control from each sample; another aliquot (200 µL) was transferred to a 96-well plate and illuminated from the top of the plates at room temperature with 10 J/cm$^2$ of UVA light at 365 nm. At the completion of illumination (or dark incubation), aliquots (100 µL) were taken from each well to determine colony-forming unit (CFU). Care was taken to ensure that the contents of the wells were mixed thoroughly before sampling, as bacteria can settle at the bottom. The aliquots were serially diluted 10-fold in pH 7.4 phosphate-buffered saline (PBS) to give dilutions of $10^{-1}$-$10^{-5}$ times in addition to the original concentration, and 10 μL aliquots of each of the dilutions were streaked horizontally on square BHI agar plates. Plates were incubated for 12-18 h at 37° C. in the dark to allow colony formation. Each experiment was performed at least three times. A control group of cells treated with light alone (no Cu-Cy added) showed the same number of CFU as an absolute control. Survival fractions were routinely expressed as ratios of the number of CFU of microbial cells treated with light and Cu-Cy (or Cu-Cy in the absence of light) to the number of CFU of microbes treated with neither.

An Amplex Red hydrogen peroxide/peroxidase assay was used to detect the production of $H_2O_2$ from Cu-Cy mediated PDT. The colorless probe Amplex Red (10-acetyl-3,7-dihydroxy phenoxazine) reacts with $H_2O_2$ in the presence of peroxidase and forms resorufin (7-hydroxy-3-Hphenoxazin-3-one). The detection process after Cu-Cy mediated PDT was according to the manufacturer's instructions. The reaction systems containing 10 μM Cu-Cy were illuminated with increasing fluence of UVA (365 nm) light, and aliquots were withdrawn and added to 50 μM Amplex Red reagent and 0.1 U/mL horseradish peroxidase (HRP) in Krebs-Ringer, phosphate (consists of 145 mM NaCl, 5.7 mM $Na_3PO_4$, 4.86 mM KCl, 0.54 mM CaCl2, 1.22 mM $MgSO_4$, 5.5 mM glucose, pH 7.35). After 30 min of incubation, a fluorescence microplate reader (excitation 530 nm; and emission 590 nm) was used to measure incremental fluorescence after an incremental fluence of 365 nm light was delivered. Groups were (1) Cu-Cy+light, (2) Amplex Red reagent alone. Each experiment was performed at least three times.

Figure 5:
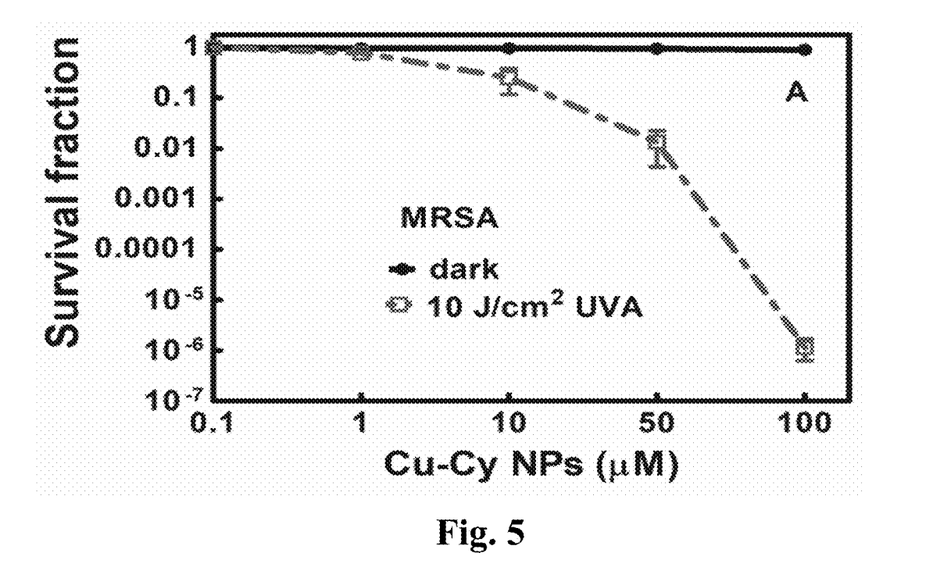
FIG. 5 shows the killing of Methicillin-resistant *Staphylococcus aureus* by amounts of Cu-Cy microparticles up to 100 µM.
Figure 6:
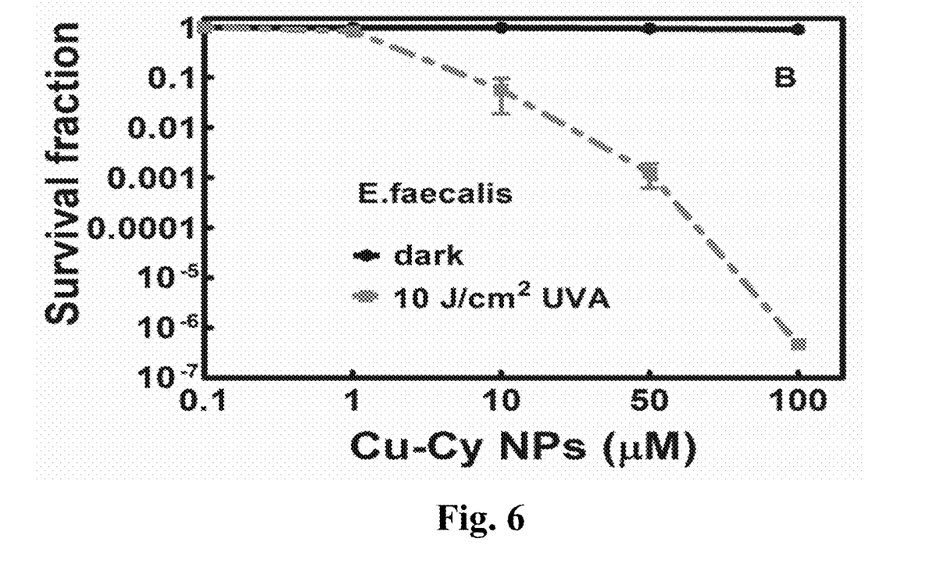
FIG. 6 shows the killing of *Enterococcus faecalis* by amounts of Cu-Cy microparticles up to 100 µM.

FIG. 5 shows the killing of Methicillin-resistant *Staphylococcus aureus* by amounts of Cu-Cy microparticles up to 100 μM vs control (no irradiation). As can be seen in FIG. 5, at 50 μM there is a 2 log reduction of these bacteria and the bacteria is effectively eliminated at 100 μM. FIG. 6 shows similar results against *Enterococcus faecalis* by amounts of Cu-Cy microparticies up to 100 μM vs control (no irradiation). As can be seen in FIG. 5, at 10 μM there was a 1 log reduction, at 50 μM there is a 3 log reduction of these bacteria and the bacteria is effectively eliminated at 100 μM.

EXAMPLE 2

The following microbial strains were used: Gram-positive bacterium, methicillin-resistant *Staphylococcus aureus* (MRSA) US300; Gram-negative bacteria, *Escherichia coli* (*E. coli*) K-12 (ATCC 33780). A colony of bacteria was suspended in 25 mL of brain heart infusion (BHI) broth (Becton, Dickinson, and Company, Franklin Lakes, NJ) and overnight in a shaker incubator (New Brunswick Scientific, Edison, NJ) under aerobic conditions at 37° C. at 120 rpm. An aliquot of 1 mL from an overnight suspension was refreshed in fresh BHI for 2 h at 37° C. to mid-log growth phase. Cell concentration was estimated by measuring optical density (OD) at 600 nm (OD of $0.8=10^8$ colony-forming unit (CFU) cells/ml). The bacterial suspension was centrifuged, washed, and re-suspended in PBS to arrest microbial growth and used ($10^8$ CFU cells/mL) again.

Suspensions of bacteria ($10^8$ cells/mL) were incubated with Cu-Cy or/and KI in dark at room temperature for 30 mins. The Cu-Cy NP concentrations were 0.1, 1, 10, and 100 μM and the concentration of KI were 0, 1, 10, 50, 100, and 200 mM, respectively. An aliquot of 100 μL was used as the dark control (DC) from each sample; another aliquot (200 μL) was transferred to a 96-well plate and illuminated from the top of the plates at room temperature with 0-10 $J/cm^2$ of UV light. After illumination (or dark incubation), aliquots (100 μL) were taken from each well to determine CFU. The contents of the wells were mixed thoroughly before sampling, as bacteria can settle at the bottom. The aliquots were serially diluted 10-fold in PBS to yield dilutions of $10^{-1}$-$10^{-5}$ times in addition to the original concentration, and 10 μL aliquots of each of the dilutions were streaked horizontally on square BHI agar plates. Plates were streaked in triplicate and incubated for 12-18 h at 37° C. in the dark to allow colony formation. Each experiment was performed at least three times. The survival fractions are expressed as the ratios of the CFU for the treated microbial cells to the CFUs of the control untreated microbes.

For singlet oxygen measurement, the RNO-ID (p-nitrosodimethylaniline (RNO)-imidazole (ID))method was used as described in the literature.[17] 0.225 mg of RNO (Sigma, USA) and 16.34 mg of ID (Sigma, USA) were added to 30 mL de-ionized (DI) water. The solution was air saturated by air bubbling for 20 min before testing. The sample solution was prepared by adding 0.5 mL of Cu-Cy (200 μM) and 0.5 mL of KI (50 mM) into 2 mL of the above RNO-ID solution. Then, the control sample solution was prepared by adding 0.5 mL of Cu-Cy (200 μM) and 0.5 mL of DI water into 2 mL of the above RNO-ID solution. Meanwhile, the two groups were exposed to UV light at 10 $J/cm^2$ for various time durations (0-8 min). The intensity of the RNO absorption peak at 440 nm was monitored using a Shimadzu UV-2450 UV-Vis spectrophotometer.

A mixture of 100 μM of Cu-Cy and 100 mM of KI were illuminated with a UV light at different intensities for 5 min and aliquots (50 μL) were taken after each illumination to measure iodine by adding starch indicator (50 μL). A microplate reader (absorbance at 610 nm) was used to measure the incremental absorbance for each illumination. The measurements were conducted on Cu-Cy with UV light and Cu-Cy+KI with UV light. Each experiment was performed three times.

For superoxide measurement, the superoxide assay NBT (20 mM), Cu-Cy NPs (10 and KI (50 mM) were dissolved in PBS. All ingredients were freshly prepared prior to the measurement. An optical microplate reader was used to measure the absorbance of the blue product (560 nm) after each UV illumination on Cu-Cy NPs and Cu-Cy NP+KI, respectively. Each experiment was repeated three times.

Figure 8:
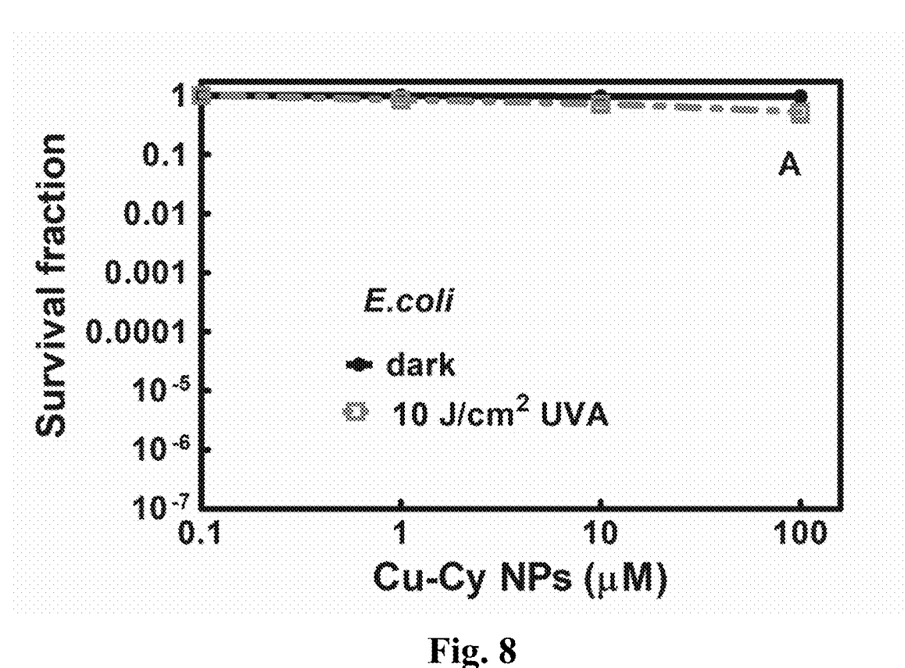
FIG. 8 demonstrates that without potassium iodide Cu-Cy has little or no effect against *E. coli*.
Figure 9:
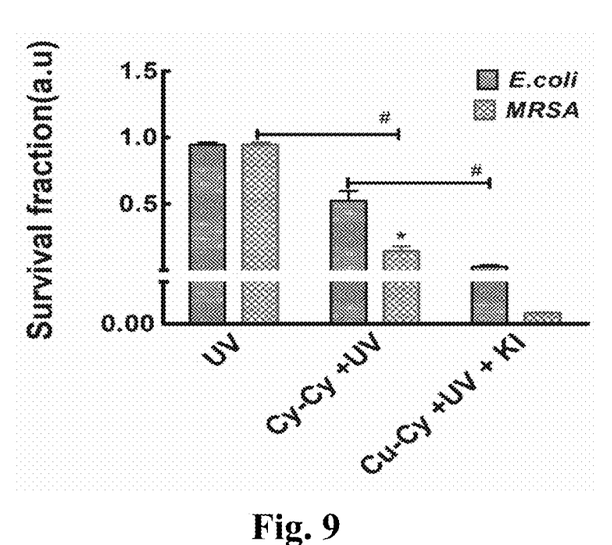
FIG. 9 demonstrates the effect of adding potassium iodide to the Cu-Cy nanoparticle composition on *E. coli* and Methicillin-resistant *Staphylococcus aureus*.

The concentration of Cu-Cy were set to be 10 or 50 μM in combination with different concentrations of KI on MRSA treatment. The result showed that at the same concentration of Cu-Cy NPs, the bactericidal effect becomes progressively stronger with the increase of the concentration of KI. There was little detectable killing without KI FIG. 8. However, the addition of 50 mM KI lead to eradication (>6 log of killing) (FIG. 9) on 50 μM Cu-Cy. However, it was just>1 log of killing for 10 μM Cu-Cy (P<0.05). The results indicate that KI can enhance the bactericidal effect of Cu-Cy NPs in aPDT.

Figure 10:
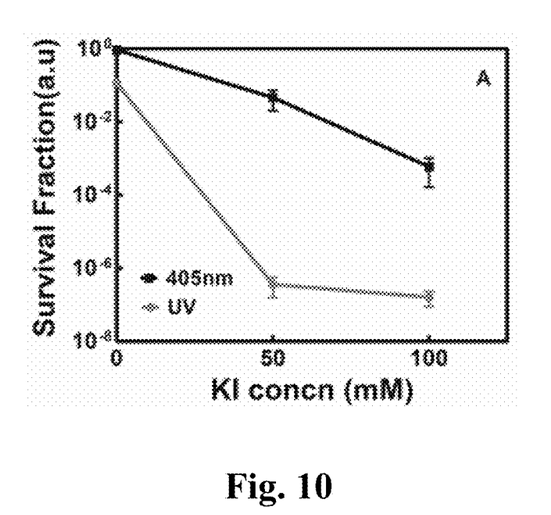
FIG. 10 shows that the killing ability of UV light source on aPDI is significantly better than that of the 405 nm.
Figure 11:
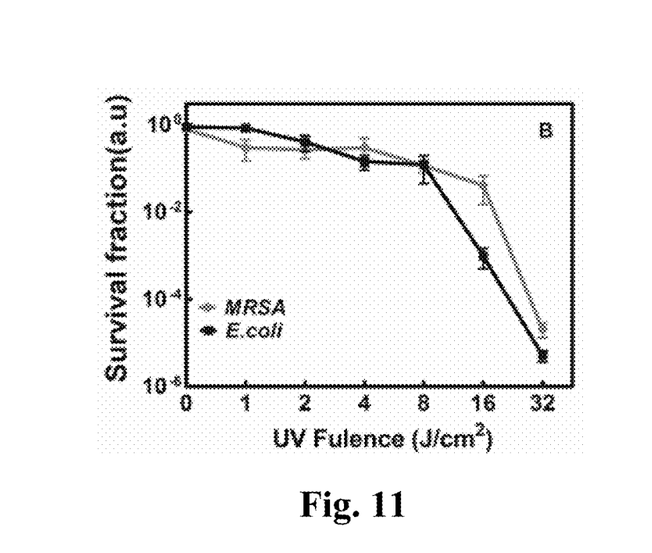
FIG. 11 shows the killing ability of Cu-Cy after adding KI was gradually enhanced with the increase of light intensity.

In order to avoid the interference of UV light itself on the sterilization effect, we used the 405 nm UV light to explore the energy parameters and then compare the sterilization ability of two different light sources. FIG. 10 shows that the killing ability of UV light source on aPDI is significantly better than that of the 405 nm. When the concentration of KI was at 0-50 mM, the killing ability was increased gradually by >6 log. When KI was at 50-100 mM, the decrease in survival was not significant, indicating that KI itself was not toxic to bacteria. When the 405 nm light source was used, the bacterial survival rate under the same conditions was only slightly decreased, and the killing decreased by <2 log during the range of KI 0-50 mM, the survival fraction decreased by 2 log at 50-100 mM. FIG. 11 shows that the killing ability of Cu-Cy after adding KI was gradually enhanced with the increase of light intensity. When the light intensity was <8 J/cm², the bactericidal ability was slowly enhanced, and the bacterial survival rate was decreased by <2 log. Similarly, when the light intensity was >8 J/cm², the survival fraction decreased to >5 log.

The excitation peak of Cu-Cy is approximately 365 nm The effect of aPDI was also related to the light intensity, and the parameter of the light energy was determined to 10 J/cm². Under these conditions, Cu-Cy NPs would be activated in the most effective way while causing little to no damage from the UV sterilization The following three groups were applied to MRSA and *E. coli* bacteria: 1) the UV group, 2) the Cu-Cy+UV group, and 3) the Cu-Cy+UV+KI group. The concentration of Cu-Cy is 50 µM. FIG. 6 shows that the survival fraction of bacteria was not significantly affected by UV light alone. However, the combination of Cu-Cy and UV irradiation led to cell death. For the Cu-Cy+UV group, the cytotoxicity is much higher on gram-positive MRSA than on gram-negative *E. coli*. (MRSA vs. *E. coli*: 0.08±0.025 vs.0.52±0.127; P<0.005). FIG. 6 also shows that after adding KI (50 mM), there was a significant increase in cell death, which enhanced to (>6 log). On MRSA (Cu-Cy only vs. Cu-Cy+KI: 0.143±0.065 vs.$e^{-9}±e^{-10}$; P=0.014<0.05); On *E. coli* (Cu-Cy only vs. Cu-Cy+KI: 0.523±0.127 vs.0.029±0.016; P<0.001). Surprisingly, when KI was added, the effect on gram-negative bacteria was almost the same as that on gram-positive bacteria (P>0.05) (MRSA vs. *E. coli*: $e^{-9}±e^{-10}$ vs. 0.029±0.016; P=0.575>0.005). When the concentration of KI was increased to 100 mM, the survival fraction of bacteria was not significantly different than that of the 50 mM concentration of KI (P>0.05). So, we may conclude that the significant cytotoxicity towards both gram-positive and gram-negative bacteria is emergent from the combination of Cu-Cy and KI together, rather than the individual components of that combination.

Because the source of electromagnetic radiation can be a topically effective source such as ultra violet radiation, wounds containing Gram-positive bacteria can be treated by non-invasive procedures. For example, a wound infected by Gram-positive bacteria can be exposed to a UV lamp. The radiation level and the time of exposure can be determined by taking a sample of the wound fluid after treatment and analyzing it for the presence, the absence or the amount of bacteria present.

The Gram-positive bacteria can be either cocci or bacilli. Non-limiting examples of Gram-positive cocci include *Streptococcus pyogenes, Streptococcus agalactiae, Streptococcus faecalis, Streptococcus pneumoniae, Staphylococcus aureus*, especially MRSA, and *Enterococcus faecalis*.

The Grain-negative bacteria can be *E. coli*.

In another aspect of the present disclosure, a method for treating a wound, comprising:
 a) identifying the presence of a bacteria in a wound;
 b) contacting the wound with the disclosed composition comprising Copper-Cysteamine nanoparticles and optionally comprising a halide salt;
 c) exposing the wound to a source of ultra violet light; and
 d) culturing a sample taken from the wound to determine the presence of the Gram-positive bacteria.

In one embodiment of this method for treating a Gram-positive bacterial wound infection the treatment can be repeated if bacteria are found to be present. In addition, based upon the initial amount present in the wound when compared to a sample taken in step (d), the physician, medical technician, etc. can adjust the UV intensity, the length of treatment or the number of treatments necessary.

A further aspect of the present disclosure relates to methods for disinfecting surfaces exposed to Gram-positive bacteria. In one embodiment the disclosed method, comprises:
 a) applying to a surface containing bacteria an effective amount of nanoparticles containing a compound having the formula:

wherein R is —CH₂CH₂NH₂ such that the Gram-positive bacteria are in contact with the compound and potassium iodide; and
 b) exposing the compound to a photo-activating amount of electromagnetic radiation at a wavelength that activates the compound.

In the case of *Enterococcus faecalis*, this bacteria presents itself commonly in hospital settings wherein patients already have compromised immune systems. The same is true with Methicillin-resistant *Staphylococcus aureus* which is extremely difficult to treat. As such, compositions comprising the Cu-Cy nanoparticles can be sprayed onto the open surfaces of a hospital environment, including operating rooms, stretchers, wheelchairs, patient rooms and the like, then the surface is irradiated by UV light to kill the bacteria.

Further disclosed are compositions comprising the disclosed Cu-Cy nanoparticles. The nanoparticles can be effectively dispersed in water. In one embodiment, to aid in dispersion of the nanoparticles, the particles can be combined with a dispersant.

The concentration of the nanoparticles in all aspects and embodiments disclosed herein can be from about 1 µM to about 100 µM. In one embodiment the concentration can be from about 1 µM to about 100 µM. In another embodiment the concentration can be from about 50 µM to about 100 µM. In a further embodiment the concentration can be from about 70 µM to about 100 µM. In a yet further embodiment the concentration can be from about 90 µM to about 100 µM. The concentration can have any value from about 1 µM to about 100 µM, for example, 1 µM, 2 µM, 3 µM, 4 µM, 5 µM, 6 µM, 7 µM, 8 µM, 9 µM, 10 µM, 11 µM, 12µ, 13 µM, 14 µM, 15 µM, 16 µM, 17 µM, 18 µM, 19 µM, 20 µM, 21 µM, 22µ, 23 µM, 24 µM, 25 µM, 26 µM, 27 µM, 28 µM, 29 µM, 30 µM, 31 µM, 32µ, 33 µM, 34 µM, 35 µM, 36 µM, 37 µM, 38 µM, 39 µM, 40 µM, 41 µM, 42µ, 43 µM, 44 µM, 45 µM, 46 µM, 47 µM, 48 µM, 49 µM, 50 µM, 51 µM, 52µ, 53 µM, 54 µM, 55 µM, 56 µM, 57 µM, 58 µM, 59 µM, 60 µM, 61 µM, 62µ, 63 µM, 64 µM, 65 µM, 66 µM, 67 µM, 68 µM, 69 µM, 70 µM, 71 µM, 72 µM, 73 µM, 74 µM, 75 µM, 76 µM, 77 µM, 78 µM, 79 µM, 80 µM, 81 µM, 82µ, 83 µM, 84 µM, 85 µM, 86 µM, 87 µM, 88 µM, 89 µM, 90 µM, 91 µM, 92µ, 93 µM, 94 µM, 95 µM, 96 µM, 97 µM, 98 µM, 99 µM, or 100 µM.

The concentration of potassium iodide in all aspects and embodiments disclosed herein can be from about 1 mM to about 100 mM. In one embodiment the concentration can be from about 1 mM to about 100 mM. In another embodiment the concentration can be from about 50 mM to about 100 mM. In a further embodiment the concentration can be from about 70 mM to about 100 mM. In a yet further embodiment the concentration can be from about 90 mM to about 100 mM. The concentration can have any value from about 1 mM, 2 mM, 3 mM, 4 mM, 5 mM, 6 mM, 7 mM, 8 mM, 9 mM 10 mM, 11 mM, 12 m, 13 mM, 14 mM, 15 mM, 16 mM, 17 mM, 18 mM, 19 mM, 20 mM, 21 mM, 22 m, 23 mM, 24 mM, 25 mM, 26 mM, 27 mM, 28 mM, 29 mM, 30 mM, 31 mM, 32 m, 33 mM, 34 mM, 35 mM, 36 mM, 37 mM, 38 mM, 39 mM, 40 mM, 41 mM, 42 m, 43 mM, 44 mM, 45 mM, 46 mM, 47 mM, 48 mM, 49 mM, 50 mM, 51 mM, 52 m, 53 mM, 54 mM, 55 mM, 56 mM, 57 mM, 58 mM, 59 mM, 60 mM, 61 mM, 62 m, 63 mM, 64 mM, 65 mM, 66 mM, 67 mM, 68 mM, 69 mM, 70 mM, 71 mM, 72 m, 73 mM, 74 mM, 75 mM, 76 mM, 77 mM, 78 mM, 79 mM, 80 mM, 81 mM, 82 m, 83 mM, 84 mM, 85 mM, 86 mM, 87 mM, 88 mM, 89 mM, 90 mM, 91 mM, 92 m, 93 mM, 94 mM, 95 mM, 96 mM, 97 mM, 98 mM, 99 mM, or 100 mM.

Porous surfaces are especially difficult to disinfect. Ire this instance a more penetrating type of electromagnetic radiation can be used.

EXAMPLE 1

In following example a 365-nm UVA light-emitting diode (LED) light source (Larson Electronics LLC, Kemp, TX) was used. The emission spectrum was measured with a spectroradiometer (SPR-01; Luzchem Research, Inc., Ottawa, Ontario, Canada) and showed a peak emission at 365±5 nm. For all experiments, the irradiance was fixed at 16 mW/cm$^2$ (1 J/cm$^2$ delivered in 1 min), measured by a model IL-1700 research radiometer-photometer (International Light, Inc., Newburyport, MA).

The following microbial strains were used: Gram-positive bacteria, methicillin-resistant *Staphylococcus aureus* (MRSA) US300 and *Enterococcus faecalis* ATCC 29212. A colony of bacteria was suspended in 10 mL of BHI and grown overnight in a shaker incubator (New Brunswick Scientific, Edison, NJ, USA) at 37° C. at 120 rpm under aerobic conditions. An aliquot of 1 mL from an overnight suspension was refreshed in fresh BHI for 2 h at 37° C. to mid-log phase. Cell concentration was estimated by measuring optical density (OD) at 600 nm (OD of 0.8=10$^8$ CFU cells/ml).

Suspensions of bacteria (10$^8$ cells/mL) were incubated with various concentrations (1 µM, 1 0 µM, 50 µM, 100 µM) of Cu-Cy in the dark at room temperature for 30 min. An aliquot of 100 µL was taken as the dark control from each sample; another aliquot (200 µL) was transferred to a 96-well plate and illuminated from the top of the plates at room temperature with 10 J/cm$^2$ of UVA light at 365 nm. At the completion of illumination (or dark incubation), aliquots (100 µL) were taken from each well to determine colony-forming unit (CFU). Care was taken to ensure that the contents of the wells were mixed thoroughly before sampling, as bacteria can settle at the bottom. The aliquots were serially diluted 10-fold in pH 7.4 phosphate-buffered saline (PBS) to give dilutions of 10$^{-1}$-10$^{-5}$ times in addition to the original concentration, and 10 µL aliquots of each of the dilutions were streaked horizontally on square BHI agar plates. Plates were incubated for 12-18 h at 37° C. in the dark to allow colony formation. Each experiment was performed at least three times. A control group of cells treated with light alone (no Cu-Cy added) showed the same number of CFU as an absolute control. Survival fractions were routinely expressed as ratios of the number of CFU of microbial cells treated with light and Cu-Cy (or Cu-Cy in the absence of light) to the number of CFU of microbes treated with neither.

An Amplex Red hydrogen peroxide/peroxidase assay was used to detect the production of $H_2O_2$ from Cu-Cy mediated PDT. The colorless probe Amplex Red (10-acetyl-3,7-dihydroxy phenoxazine) reacts with $H_2O_2$ in the presence of peroxidase and forms resorufin (7-hydroxy-3H-phenoxazin-3-one). The detection process after Cu-Cy mediated PDT was according to the manufacturer's instructions. The reaction systems containing 10 µM Cu-Cy were illuminated with increasing fluence of UVA (365 nm) light, and aliquots were withdrawn and added to 50 µM Amplex Red reagent and 0.1 U/mL horseradish peroxidase (HRP) in Krebs-Ringer, phosphate (consists of 145 mM NaCl, 5.7 mM $Na_3PO_4$, 4.86 mM KCl, 0.54 mM CaCl2, 1.22 mM $MgSO_4$, 5.5 mM glucose, pH 7.35). After 30 min of incubation, a fluorescence microplate reader (excitation 530 nm; and emission 590 nm) was used to measure incremental fluorescence after an incremental fluence of 365 nm light was delivered. Groups were (1) Cu-Cy+light, (2) Amplex Red reagent alone. Each experiment was performed at least three times.

FIG. 5 shows the killing of Methicillin-resistant *Staphylococcus aureus* by amounts of Co-Cy microparticles up to 100 µM vs control (no irradiation). As can be seen in FIG. 5, at 50 µM there is a 2 log reduction of these bacteria and the bacteria is effectively eliminated at 100 µM. FIG. 6 shows similar results against *Enterococcus faecalis* by amounts of Cu-Cy microparticles up to 100 µM vs control (no irradiation). As can be seen in FIG. 5, at 10 µM there was a 1 log reduction, at 50 µM there is a 3 log reduction of these bacteria and the bacteria is effectively eliminated at 100 µM.

EXAMPLE 2

The following microbial strains were used: Gram-positive bacterium, methicillin-resistant *Staphylococcus aureus* (MRSA) US300; Gram-negative bacteria, *Escherichia coli* (*E. coli*) K-12 (ATCC 33780). A colony of bacteria was suspended in 25 mL of brain heart infusion (BHI) broth (Becton, Dickinson, and Company, Franklin Lakes, NJ) and overnight in a shaker incubator (New Brunswick Scientific, Edison, NJ) under aerobic conditions at 37° C. at 120 rpm. An aliquot of 1 mL from an overnight suspension was refreshed in fresh BHI for 2 h at 37° C. to mid-log growth phase. Cell concentration was estimated by measuring optical density (OD) at 600 nm (OD of 0.8=10$^8$ colony-forming unit (CFU) cells/ml). The bacterial suspension was centrifuged, washed, and re-suspended in PBS to arrest microbial growth and used (10$^8$ CFU cells/mL) again.

Suspensions of bacteria (10$^8$ cells/mL) were incubated with Cu-Cy or/and KI in dark at room temperature for 30 mins. The Cu-Cy NP concentrations were 0.1, 1, 10, and 100 µM and the concentration of KI were 0, 1, 10, 50, 100, and 200 mM, respectively. An aliquot of 100 µL was used as the dark control (DC) from each sample; another aliquot (200 µL) was transferred to a 96-well plate and illuminated from the top of the plates at room temperature with 0-10 J/cm$^2$ of UV light. After illumination (or dark incubation), aliquots (100 µL) were taken from each well to determine CFU. The contents of the wells were mixed thoroughly before sampling, as bacteria can settle at the bottom. The aliquots were serially diluted 10-fold in PBS to yield dilutions of 10$^{-1}$-10$^{-5}$ times in addition to the original concentration, and 10 µL aliquots of each of the dilutions were streaked horizontally on square BHI agar plates. Plates were streaked in triplicate and incubated for 12-18 h at 37° C. in the dark to allow colony formation. Each experiment was performed at least three times. The survival fractions are expressed as the ratios of the CFU for the treated microbial cells to the CFUs of the control untreated microbes.

For singlet oxygen measurement, the RNO-ID (p-nitrosodimethylaniline (RNO)-imidazole (ID))method was used as described in the literature.[17] 0.225 mg of RNO (Sigma, USA) and 16.34 mg of ID (Sigma, USA) were added to 30 mL de-ionized (DI) water. The solution was air saturated by air bubbling for 20 min before testing. The sample solution was prepared by adding 0.5 mL of Cu-Cy (200 μM) and 0.5 mL of KI (50 mM) into 2 mL of the above RNO-ID solution. Then, the control sample solution was prepared by adding 0.5 mL of Cu-Cy (200 μM) and 0.5 mL of DI water into 2 mL of the above RNO-ID solution. Meanwhile, the two groups were exposed to UV light at 10 J/cm² for various time durations (0-8 min). The intensity of the RNO absorption peak at 440 nm was monitored using a Shimadzu UV-2450 UV-Vis spectrophotometer.

A mixture of 100 μM of Cu-Cy and 100 mM of KI were illuminated with a UV light at different intensities for 5 min and aliquots (50 μL) were taken after each illumination to measure iodine by adding starch indicator (50 μL). A microplate reader (absorbance at 610 nm) was used to measure the incremental absorbance for each illumination. The measurements were conducted on Cu-Cy with UV light and Cu-Cy+KI with UV light. Each experiment was performed three times.

For superoxide measurement, the superoxide assay NBT (20 mM), Cu-Cy NPs (10 and KI (50 mM) were dissolved in PBS. All ingredients were freshly prepared prior to the measurement. An optical microplate reader was used to measure the absorbance of the blue product (560 nm) after each UV illumination on Cu-Cy NPs and Cu-Cy NP+KI, respectively. Each experiment was repeated three times.

The concentration of Cu-Cy were set to be 10 or 50 μM in combination with different concentrations of KI on MRSA treatment. The result showed that at the same concentration of Cu-Cy NPs, the bactericidal effect becomes progressively stronger with the increase of the concentration of KI. There was little detectable killing without KI FIG. 8. However, the addition of 50 mM KI lead to eradication (>6 log of killing) (FIG. 9) on 50 μM Cu-Cy. However, it was just>1 log of killing for 10 μM Cu-Cy (P<0.05). The results indicate that KI can enhance the bactericidal effect of Cu-Cy NPs in aPDT.

In order to avoid the interference of UV light itself on the sterilization effect, we used the 405 nm UV light to explore the energy parameters and then compare the sterilization ability of two different light sources. FIG. 10 shows that the killing ability of UV light source on aPDI is significantly better than that of the 405 nm. When the concentration of KI was at 0-50 mM, the killing ability was increased gradually by >6 log. When KI was at 50-100 mM, the decrease in survival was not significant, indicating that KI itself was not toxic to bacteria. When the 405 nm light source was used, the bacterial survival rate under the same conditions was only slightly decreased, and the killing decreased by <2 log during the range of KI 0-50 mM, the survival fraction decreased by 2 log at 50-100 mM. FIG. 11 shows that the killing ability of Cu-Cy after adding KI was gradually enhanced with the increase of light intensity. When the light intensity was <8 J/cm², the bactericidal ability was slowly enhanced, and the bacterial survival rate was decreased by <2 log. Similarly, when the light intensity was >8 J/cm², the survival fraction decreased to >5 log.

The excitation peak of Cu-Cy is approximately 365 nm The effect of aPDI was also related to the light intensity, and the parameter of the light energy was determined to 10 J/cm². Under these conditions, Cu-Cy NPs would be activated in the most effective way while causing little to no damage from the UV sterilization

The following three groups were applied to MRSA and *E. coli* bacteria: 1) the UV group, 2) the Cu-Cy+UV group, and 3) the Cu-Cy+UV+KI group. The concentration of Cu-Cy is 50 μM. FIG. 6 shows that the survival fraction of bacteria was not significantly affected by UV light alone. However, the combination of Cu-Cy and UV irradiation led to cell death. For the Cu-Cy+UV group, the cytotoxicity is much higher on gram-positive MRSA than on gram-negative *E. coli*. (MRSA vs. *E. coli*: 0.08±0.025 vs.0.52±0.127; P<0.005). FIG. 6 also shows that after adding KI (50 mM), there was a significant increase in cell death, which enhanced to (>6 log). On MRSA (Cu-Cy only vs. Cu-Cy+KI: 0.143±0.065 vs.$e^{-9} \pm e^{-19}$; P=0.014<0.05); On *E. coli* (Cu-Cy only vs. Cu-Cy+KI: 0.523±0.127 vs.0.029±0.016; P<0.001). Surprisingly, when KI was added, the effect on gram-negative bacteria was almost the same as that on gram-positive bacteria (P>0.05) (MRSA vs. *E. coli*: $e^{-9} \pm e^{-10}$ vs. 0.029±0.016; P=0.575>0.005). When the concentration of KI was increased to 100 mM, the survival fraction of bacteria was not significantly different than that of the 50 mM concentration of KI (P>0.05). So, we may conclude that the significant cytotoxicity towards both gram-positive and gram-negative bacteria is emergent from the combination of Cu-Cy and KI together, rather than the individual components of that combination.

Figure 12:
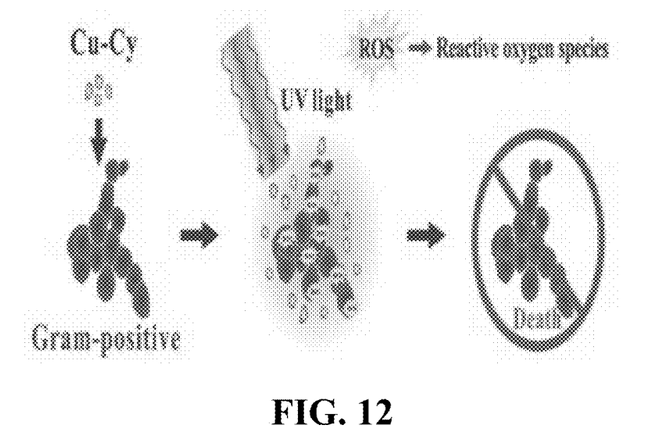
FIG. 12 depicts the mechanism of bacterial kill.

FIG. 12 depicts the mechanism of bacterial kill. Cu-Cy is injected into the site of bacterial growth, for example, a wound. Electromagnetic radiation (UV light in this example) is directed to the Cu-Cy/bacteria complex wherein reactive oxygen species are formed which kill the bacteria.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A method for treating a bacterial infection in a subject, comprising:
    a) administering to a subject having a bacterial infection an effective amount of nanoparticles containing a compound having the formula:

wherein R is —CH₂CH₂NH₂ such that the bacteria are in contact with the compound; and
    b) exposing the compound to a photo-activating amount of electromagnetic radiation at a wavelength that activates the compound.

2. The method according to claim 1, wherein the bacteria is a gram positive bacteria.

3. The method according to claim 1, wherein the bacteria is chosen from *Streptococcus pyrogenes, Streptococcus agalactiae, Streptococcus faecalis, Streptococcus pneumoniae, Staphylococcus aureus*, Methicillin-resistant *Staphylococcus aureus*, and *Enterococcus faecalis*.

4. The method according to claim 1, wherein the source of radiation is chosen from ultra violet rays, microwave radiation, an X-ray source, a gamma-ray source, a beta-ray source, a source of proton emission, a source of electron emission, or a source of neutron emission.

5. The method according to claim 1, wherein the concentration of compound administered is from about 1 μM to about 100 μM.

6. The method according to claim 1, wherein the compound is administered more than once.

\* \* \* \* \*